(12) United States Patent
Bru-Magniez et al.

(10) Patent No.: US 6,610,078 B1
(45) Date of Patent: Aug. 26, 2003

(54) SUTURE MATERIAL FOR WOUNDS BASED ON METHYLIDENE MALONATE

(75) Inventors: Nicole Bru-Magniez, Paris (FR); Pascal Breton, Tigy (FR); Claude Roques-Carmes, Besancon (FR); Isabelle Beliard, Toronto (CA)

(73) Assignee: Virsol, Paris (FR)

(*) Notice: Subject to any disclaimer, the term of this patent is extended or adjusted under 35 U.S.C. 154(b) by 0 days.

(21) Appl. No.: 09/509,830

(22) PCT Filed: Feb. 9, 2000

(86) PCT No.: PCT/FR00/00305
§ 371 (c)(1),
(2), (4) Date: Jul. 5, 2000

(87) PCT Pub. No.: WO00/47242
PCT Pub. Date: Aug. 17, 2000

(30) Foreign Application Priority Data

Feb. 9, 1999 (FR) .............................................. 99 01485

(51) Int. Cl.$^7$ .............................................. A61B 17/08
(52) U.S. Cl. ........................ 606/214; 606/215; 128/898
(58) Field of Search ................................. 606/213–215, 606/76, 77; 128/898; 523/118; 424/78.35, 422, 423

(56) References Cited

U.S. PATENT DOCUMENTS

| 5,328,687 A | * | 7/1994 | Leung et al. ............ 424/78.35 |
| 5,550,172 A | * | 8/1996 | Regula et al. ................. 606/76 |
| 5,575,997 A | | 11/1996 | Leung et al. |
| 5,624,669 A | | 4/1997 | Leung et al. |
| 6,106,807 A | | 8/2000 | Albayrak et al. |
| 6,211,273 B1 | | 4/2001 | Bru-Magniez et al. |

FOREIGN PATENT DOCUMENTS

| FR | 2722411 | 1/1996 |
| WO | 96/00760 | 1/1996 |

* cited by examiner

Primary Examiner—Julian W. Woo

(74) Attorney, Agent, or Firm—Dennison, Schultz & Dougherty

(57) ABSTRACT

A method for the suture of wounds, includes applying a sufficient quantity of a biocompatible, bio-adhesive mixture with at least 50% by weight of a methylidene malonate-based composition containing:

40 to 100% by weight of at least one methylidene malonate of formula (I):

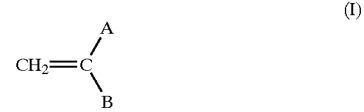

in which:
A and B independently represent a group (a) or (b):

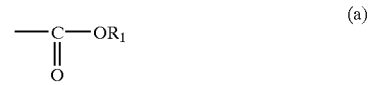

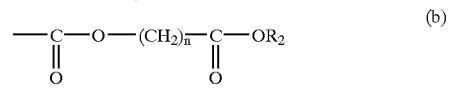

in which $R_1$ and $R_2$ independently represent a linear or branched alkyl group with 1 to 6 carbon atoms, n is an integer between 1 and 5, and at least one of A and B represents a (b) group;

and/or one or more methylidene malonate oligomers with a molecular weight less than or equal to 6,000 and including recurrent units of formula (II):

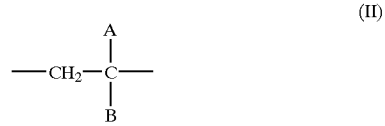

in which A and B are as defined above; and 0 to 60% by weight of at least one methylidene malonate polymer with a molecular weight greater than 6,000 and including recurrent units of formula (II).

32 Claims, No Drawings

SUTURE MATERIAL FOR WOUNDS BASED ON METHYLIDENE MALONATE

BACKGROUND OF THE INVENTION

The present invention relates to a new methylidene malonate-based material for the suture of wounds.

Within the present description, the term "suture material" refers to a bicompatible material that, by adhesion, lets the sides of wounds be brought together, stops bleeding (hemostasis) and favours the cicatrisation of injured tissue.

The invention mainly applies to the treatment of epidermic, dermo-epidermic or hypo-dermo-epidermic wounds, in particular clean dermo-epidermic wounds.

There are now four main ways for doctors to treat dermo-epidermic wounds, suture by resorbable or non-resorbable thread (stitches), the use of staples, the use of adhesive strips or the use of cutaneous glues.

Suture with thread is generally used to bring together the superficial dermic and epidermic layers, in the case of non resorbable thread, or to bring together the deep muscular and hypodermic layers in the case of resorbable thread.

This is the method of treatment most commonly used.

However, it is relatively difficult to use since it requires a local anaesthetic, sterile associated instruments (forceps, scissors, needle holder . . . ), nursing care after the treatment as well as the removal of the stitches several days later.

Although this is not too limiting during the post-surgical period, this is not the case during the treatment of post-traumatic wounds in the doctor's office or emergency ward.

In addition, this type of treatment is more or less psychologically traumatic for the patient, especially if the patient is a child, in which case fast and painless treatment is warranted.

In practice, the use of staples pretty much involves the same problems as the suture with thread.

The use of adhesive strips, such as for example the product known under the trade name Steri-Strip® is used to treat benign wounds almost without pain.

However, its use is limited to the treatment of small dermo-epidermic wounds (about one centimeter) outside of any body area likely to be subject to mechanical stress.

Over the last few years, different adhesive biocompatible materials have been developed for the suture of wounds.

These adhesive materials are generally called "glues" and can be divided into two categories:
biological adhesives, generally synthesised from plasma proteins;
synthetic adhesives, mainly made of cyanoacrylate, and in particular, 2-octylcyanoacrylate, 2-ethylcyanoacrylate, 2-butylcyanoacrylate and 2-isobutylcyanoacrylate.

Biological adhesives were chosen to reproduce the last phase of coagulation and anchor the clot to the tissue by providing fibronectin ("junction protein") on the cicatrisation sites.

These biological adhesives are particularly advantageous since they are used to again interlock the injured tissue and allow for the growth of the cicatrisation tissue.

However, the main disadvantage is the underlying risk of viral transmission.

Synthetic adhesives are particularly advantageous since:
they generally come in ready-to-use form;
they can be used to suture varying sizes of wounds (from about 1 to 10 cm); and the aesthetic quality of the scars after suture appears as good as or better than the scars obtained with a suture by thread or staples.

However, the synthetic adhesives currently available on the market have a great many disadvantages.

First, the adhesives are generally liquid and, applied only on the surface, tend to drip beyond their zone of application.

Second, these adhesives are generally potentially allergenic and decompose with great difficulty in the organism, generally forming products considered to be toxic for the organism. This considerably limits their value.

SUMMARY OF THE INVENTION

In these conditions, he purpose of the present invention is to solve a technical problem consisting of the provision of a novel material for the suture of wounds, that is essentially synthetic, that has the same advantages as the aforementioned synthetic adhesives, that is easy to use, can decompose relatively easy in the organism without producing toxic products and that can be applied inside the wound in all of the layers of the damaged skin.

The present invention also aims at solving the aforementioned technical problem in a way applicable on an industrial scale.

It was discovered, and this is the basis of the present invention, that certain monomer and/or oligomer and/or polymer compositions made of methylidene malonate have all of the properties required, in particular in terms of bio-adhesion and viscosity before and/or after application, for the creation of new materials for the suture of wounds complying with this goal.

DETAILED DESCRIPTION OF THE INVENTION

Therefore, according to a first aspect, the purpose of the present invention is a material for the suture of wounds consisting of a biocompatible, bio-adhesive mixture containing at least 50% by weight, and preferably 80% by weight of a methylidene malonate-based composition containing:

40 to 100% by weight, and preferably 50 to 100% by weight of one or more methylidene malonates of formula (I)

in which:
A and B independently represent a group (a) or (b):

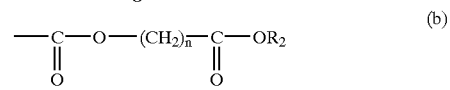

in which $R_1$ and $R_2$ independently represent a linear or branched alkyl group with 1 to 6 carbon atoms, and n is an integer from 1 to 5;
and/or one or more methylidene malonate oligomers with a molecular weight less than or equal to 6,000 and consisting of recurrent units of formula (II):

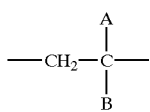

(II)

in which A and B are as defined above;

0 to 60% by weight, and preferably 0 to 50% by weight of one or more methylidene malonate polymers with a molecular weight greater than 6,000 and consisting of recurrent units of formula (II).

According to a specific feature of the invention, in aforementioned formulae (I) and (II):

A represents a group (a) in which $R_1$ represents an alkyl group with 1 to 6 carbon atoms, preferably an ethyl group, B represents a group (b) in which $R_2$ represents an alkyl group with 1 to 6 carbon atoms, preferably an ethyl group, and n is a number equal to 1.

In a preferred embodiment of the invention, the aforementioned methylidene malonate composition contains:

50 to 90% by weight of one or more methylidene malonate oligomers with a molecular weight less than or equal to 6,000, preferably less than or equal to 3,000 and consisting of recurrent units of formula (II), 10 to 50% by weight of one or more methylidene malonate polymers with a molecular weight greater than 6,000, and the aforementioned material has a glass transition temperature that less than or equal to 0° C., preferably between −10 and −35° C., and still preferably between −20 and −30° C.

This composition is novel as such and this application also aims at protecting it as a novel material.

In a currently preferred embodiment of the invention, the aforementioned methylidene malonate-based composition contains:

55 to 65% by weight of one or more methylidene malonate oligomers with a molecular weight less than or equal to 3,000, and preferably between 300 and 1,000 and consisting of recurrent units of formula (II), 35 to 45% by weight of one or more methylidene malonate polymers with a molecular weight greater than 6,000, preferably greater than 9,000, and preferably between 12,000 and 25,000.

Thereby, the material for the suture of wounds that complies with the present invention is essentially characterised by the fact that it mainly consists of a methylidene malonate-based composition that itself mainly consists of monomer(s) and/or oligomer(s) whose molecular weight is less than or equal to 6,000, preferably less than or equal to 3,000.

The viscosity and bio-adhesion (or bonding) properties of such a composition enables its use in the treatment of dermo-epidermic wounds, alone or in a mixture with other biocompatible compounds.

In particular, it has been observed that such a composition may be applied within the wound, without any persistent bleeding noted during adhesion, and without any inflammatory reaction noted after 10 days of adhesion.

In addition, the methylidene malonate-based compositions that can be used in the invention, are degradable by bio-erosion, releasing ethanol and glycolic acid that are generally not considered to be toxic for the organism. Glycolic acid even seems to act like a stimulator of cell growth.

These methylidene malonate-based compositions may be easily prepared by the skilled man, optionally by the simple mixing of these compounds prepared separately (monomer (s), oligomer(s), polymer(s)) in an appropriate solvent, and the subsequent evaporation of the solvent.

The methylidene malonate monomers can be prepared according to the method described in patent EP 0,283,346 corresponding to patents U.S. Pat. No. 4,931,584 and U.S. Pat. No. 5,142,098 herein incorporated by reference, after vacuum degassing by a pallet pump to constant weight in order to remove the polymerisation inhibitor ($SO_2$).

Methylidene malonate oligomers and polymers can be synthesized by anionic or radical polymerisation from the aforementioned monomers.

In the case of preferred methylidene malonate-based compositions, that are formed from a mixture of oligomer(s) and polymer(s), these compositions may also be obtained in one single step. The relative proportions of constituents can be adjusted by varying the concentration in anionic or radical initiator in the polymerisation medium.

The skilled man can easily adjust the aforementioned physico-chemical characteristics of the methylidene malonate-based compositions, to obtain a material for the suture of wounds that has the required characteristics of bio-adhesion and viscosity.

As understood, the physico-chemical characteristics have to be adjusted according to the nature of all of the components in the suture material. The goal is to obtain a bio-adhesive material with the appropriate viscosity.

In general, the constituents of the material for the suture of wounds complying with the invention, other than the aforementioned methylidene malonate-based composition, may account for up to 50% of the weight of this material.

Of course, these constituents will be chosen so as to form, with the aforementioned methylidene malonate-based compositions, intimate mixtures with the desired characteristics of bio-adhesion and viscosity.

Preferably, when present, these constituents only account for about 1 to 20%, more preferably 1 to 10% by weight of the total weight of the suture material.

These constituents may be varied, from natural or synthetic origin.

By way of example of such constituents, mention will be made of:

soluble or insoluble substituted functionalised dextrans that are more particularly described in patents FR n° 2,555,589 and FR n° 2,461,724:

polycyanoacrylates, preferably polyalkylcyanoacrylates;

polyalkylmethylacrylates;

biocompatible polyurethanes;

polyoxyalkylenes;

polyaminoacids;

polylactates;

polylactate-co-glycolates;

polyvinylalcohols.

Additional preferred constituents are, for example, polyethylene glycol, a hydrophilic additive belonging to the family of polyoxyalkylenes able to play a role as plasticiser within the mixture, or even poly(lactide-co-glycolide), a biodegradable additive belonging to the family of polylactate-co-glycolates able to improve the biodegradability of the mixture.

In general, these constituents will be present within the suture material in the form of mixtures with the aforementioned methylidene malonate-based compositions.

It should be noted that, without leaving the context of the present invention, these constituents may also be found within the suture material in the form of monomer units in copolymers including methylidene malonate units of formula (II), as defined above.

These methylidene malonate copolymers can be prepared by the classic polymerisation techniques well-known to the person skilled in the art. Among them, mention is made of anionic polymerisation, radical polymerisation or even the technique of coupling the precursor sequences of the copolymer, these sequences having been adequately functionalised beforehand on the chain end.

In general, the monomer units forming the aforementioned constituents will be chosen from among the constituent monomer units of polyacrylates, polysaccharides, polyoxyalkylenes, polylactates and polylactate-co-glycolates.

Among the constituent monomer units of polysaccharides able to be used in the context of the invention, mention can in particular be made of the constituent monomer units of soluble or insoluble substituted functionalised dextrans that are in particular described in patents FR n° 2,555,589 and FR n° 2,461,724.

Among the constituent monomer units of polyacrylates able to be used in the context of the invention, mention will be made of alkylcyanoacrylates, alkyl methacrylates and itaconates.

In general, at least 50% of the monomer units of the methylidene malonate-based copolymers used in the present invention will consist of methylidene malonate units.

These copolymers may be random or present block or grafted structures.

The suture material complying with the present invention may, if necessary, include biocompatible products able to adjust its viscosity among the constituents, like, for example, plasticisers or even biocompatible products that improve the adhesion like, for example, so-called "tackifying" resins.

Among the plasticisers suitable for the present invention, mention will be made, for example, of the esters derived from adipic acid, azelaic acid, citric acid, oleic acid, stearic acid, sebacic acid; polyethylene glycol.

Among the suitable tackifying resins which are suitable within the context of the present invention, mention the modified polyterpine or terpine resins, hydrocarbon resins, and mixtures of aromatic and aliphatic resins.

The suture material, in compliance with the present invention, may also include one or more active principles among the constituents, mainly chosen from among the local anaesthetics, such as lidocaine; bacteriostatic agents and antibiotic agents, such as, for example, streptomycin; analgesics, like, for example, ketoprofen.

According to a second aspect, the purpose of the present invention is a treatment method for epidermic, dermo-epidermic, hypo-dermo-epidermic wounds characterised in that it consists of applying a sufficient quantity of material for the suture of wounds within the aforementioned wound, as defined above, if necessary previously preheated to a temperature above the softening temperature.

In the case of the preferred materials, mainly consisting of methylidine malonate-based compositions formed from a mixture of oligomers and polymers with a glass transition temperature between 0 and −50° C., the aforementioned preheating temperature is in the order of about 35° C. to 47° C.

As understood, the suture material complying with the present invention, will be packaged in a form enabling its application, like, for example, inside a self-heating syringe.

The present invention will now be illustrated by the following non-limiting examples.

The following abbreviations have been used in these examples:

MM 2.1.2: methylidene malonate complying with the formula:

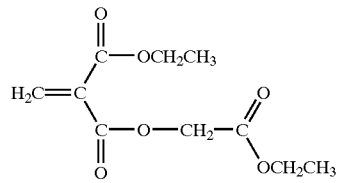

also called: 1-ethoxycarbonyl-1-ethoxycarbonylmethyleneoxycarbonyl ethene

PMM 2.1.2: oligomer or polymer consisting of recurrent monomer units complying with the formula

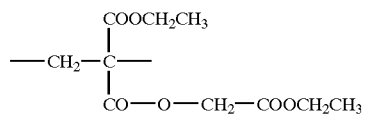

PEG: poly(ethyleneglycol)
PLGA: poly(lactide-co-glycolide)
POE: poly(oxyethylene)
PϵCL: poly(ϵcaprolactone)
DCC: dicyclohexylcarbodiimide In addition, in these examples as well as in the description, "molecular weight" refers to the average molar mass by weight, referred to as $M_w$, expressed in g/mole of polystyrene (PS) equivalent, and measured by Gel Permeation Chromatography (GPC) with chromatography equipment standardised with polystyrene reference polymers.

In addition, the glass transition temperature (Tg) was determined by differential enthalpic analysis with a scanning speed of 10° C. per minute.

EXAMPLE 1

Preparation of a Material for the Suture of Wounds Complying With the Invention

A. Experimental Protocol

Various methylidene malonate-based compositions formed from mixtures of oligomers and polymers were prepared by anionic polymerisation (0.1 N NaOH) in solvent medium (acetone) from the monomer, in accordance with the following procedure:

in a 250 ml round-bottomed-flask, a quantity m of monomer (expressed in grams), maintained under primary vacuum, for 5 hours in order to eliminate the polymerisation inhibitor (sulphur dioxide) and dissolved in a volume V (expressed in milliliters) of acetone is maintained under magnetic stirring for 10 minutes.

then a volume V' (expressed in milliliters) of 0.1 N sodium hydroxide solution is added all at once, still under magnetic stirring.

The stirring is maintained for about 15 minutes, then the polymerisation is stopped (if it hasn't already terminated) by the addition of decimolar hydrochloric acid in a volume roughly identical to the volume of sodium hydroxide solution. The acetone is evaporated off under vacuum and the polymer obtained is washed with distilled water and then dried over silica gel.

Alternatively, it is possible to prepare these compositions by adding the monomer solution in acetone to a solution of sodium hydroxide also in acetone.

B. Characteristics of the Prepared Compositions

The experimental conditions used in the preparation of five methylidene malonate-based compositions as well as the glass transition temperature (Tg) of these compositions are indicated in Table I below.

TABLE I

| Composition No. | m (g) MM2.1.2 | V (ml) of acetone | V' (ml) NaOH | Tg (° C.) |
|---|---|---|---|---|
| 1 | 1 | 50 | 10 | −22 |
| 2 | 3 | 150 | 30 | −20 |
| 3 | 1 | 50 | 2.6 | −13 |
| 4 | 1 | 50 | 2.6 | −11 |
| 5 | 3 | 150 | 3 | −10 |

About 80% of the weight of composition 1 consists of oligomers with a molecular weight less than 3,000 (Mw=about 600), and about 20% of the weight consists of polymers where the major component of which represents a molecular weight of 10,500.

About 78% of the weight of composition 2 consists of oligomers with a molecular weight less than 3,100, and about 22% of the weight consists of polymers the major component of which represents a molecular weight of 13,000.

About 78% of the weight of composition 5 consists of oligomers with a molecular weight less than 5,100 and about 22% of the weight consists of polymers the major component of which represents a molecular weight of about 18,000.

A study carried out on flaps of human skin obtained from surgical wastes on abdominoplasties has enabled confirming that all of these compositions have all of the qualities required, in particular in terms of bio-adhesion and viscosity, to be used as suture material, either alone or in association with other bio-compatible constituents, as defined above.

In particular, the adhesive power of the aforementioned five methylidene malonate-based compositions was found to be stable after 24 hours without any difference noted between bonded wounds and bonded-stripped wounds.

In addition, a small quantity of composition was found to be sufficient for a satisfactory adhesive power when both sides of the wound are brought together manually after application of the said composition.

The best results were obtained with composition 1.

When such compositions are intended to be used alone, the glass transition temperature has to be less than 0° C., in order to prevent these compositions from hardening too quickly before the application inside the wound.

Advantageously, this glass transition temperature will be between −10 and −35° C., and preferably between −20° C. and −30° C.

Preparation of Other Materials for the Suture of Wounds Complying With the Invention A/Experimental Protocol Different methylidene malonate-based compositions formed from mixtures of oligomers and polymers and incorporating optionally one or more additional components have been prepared by the simple mixing of these components in an appropriate solvent.

More specifically, methylidene malonate oligomers, methylidene malonate polymers and optionally one additional component are weighed out in pre-determined amounts and solubilized in a common solvent (generally in acetone) under magnetic stirring, then the solvent is evaporated using a rotary evaporator and the mixture is dried in a primary vacuum dessicator.

B/Characteristics of the Prepared Compositions

The main characteristics of the prepared compositions are indicated in Table IA below.

Compositions 6 and 7 are constituted solely of methylidene malonate 2.1.2 oligomers and methylidene malonate 2.1.2 polymers.

Compositions 8 and 9 further comprise a hydrophilic additive which is of the PEG type and has a low molecular weight which can be used as plasticizer in the mixture.

Compositions 10 and 11 further comprise a biodegradable additive of the PLGA type which can be used to improve the biodegradability of the mixture.

The PLGA used has the following features:
Mw=50,000–70,000; Tg=45–50° C. (Aldrich 43,044-7)

Composition 11 further comprises a part which is made of methylidine malonate 2.1.2 monomers, this monomer being added in the cold to a mixture in acetone consisting of the three other components.

Compositions 12 and 13 further comprise an amphiphilic additive which is based on methylidene malonate 2.1.2 and which has a very good affinity with other components and can be used to improve the adhesive resistance on the wound.

This amphiphilic additive is a block copolymer having 250 ethylene oxyde units and 43 MM 2.1.2. units, and has been prepared by successive anionic polymerisation of the ethylene oxyde and then of the MM 2.1.2.

Composition 14 comprises an additional biodegradable additive based on MM 2.1.2. which is a copolymer of PMM 2.1.2 PϵCL which has a good affinity with the mixture and has a biodegradable sequence which enables modulating the overall degradability kinetics of said mixture.

This additive is a block copolymer having a PMM2.1.2 sequence of 5,800 g/mole and a PϵCL sequence of 2,000 g/mole which has been prepared by chemical coupling between both homopolymers, α-hydroxy functionalized PMM2.1.2 and α-carboxy functionalized PϵCL in the presence of DCC in dichloromethane.

TABLE IA

| Composition No. | Mw* oligomers of MM2.1.2. (g/mol) | Mw* PMM2.1.2. (g/mol) | Nature of the additive | Mass composition oligomers/ PMM2.1.2./ additives | Tg of the mixture (° C.) |
|---|---|---|---|---|---|
| 6 | 1950 | 29 300 | | 91/9 | −26.9 |
| 7 | 700 | 15 000 | | 60/40 | −15 |
| 8 | 1950 | — | PEG750 | 95/0/5 | −22.3 |
| 9 | 1950 | 34 700 | PEG550 | 80/16/4 | −31.3 |
| 10 | 2200 | — | PLGA | 95/0/5 | −34.2 |
| 11 | 1450 | 60 500 | MM2.1.2./PLGA | 60/30/5/5 | −41.7 |

TABLE IA-continued

| Composition No. | Mw* oligomers of MM2.1.2. (g/mol) | Mw* PMM2.1.2. (g/mol) | Nature of the additive | Mass composition oligomers/ PMM2.1.2./ additives | Tg of the mixture (° C.) |
|---|---|---|---|---|---|
| 12 | 2200 | — | POE-PMM2.1.2. | 95/0/5 | −45.1 |
| 13 | 1450 | 60 500 | MM2.1.2./POE-PMM2.1.2. | 60/30/5/5 | −44.4 |
| 14 | 1450 | | PϵCL-PMM2.1.2 | 91/9 | −22.7 |

*PS equivalent.

EXAMPLE 2

Demonstration of the Value of Methylidene Malonate-based Compositions as an Essential Constituent in a Material to Suture Wounds The adhesive power of methylidene malonate-based compositions was confirmed in an in vivo study on dermo-epidermic scars in the guinea pig.

This study was carried out with aforementioned composition 1 that has a glass transition-temperature of −22° C., and in parallel versus a reference system (suture with non-resorbable thread).

The following protocol was used.

The animals used were male Hartley guinea pigs (n=10) weighing 250–300 g (Charles Rivers, France) free of all viral, bacterial, fungal and parasitic disease.

All of the guinea pigs were first shaved after a three-day period of acclimatisation in P 3,000 rabbit cages (IFFA CREDO, France).

Five of them were selected at random and underwent:
- a—disinfection with foaming Bétadine for a second shave (final close shave),
- b—general anaesthetic for 3 minutes with Halothane (3%) with a flow of oxygen of 3 l.min$^{-1}$ (ACOMA VAPORIZER®, Japan),
- c—a second supplementary disinfection with yellow Bétadine,
- d—a dermo-epidermic paravertebral incision about 1 cm long, with a No. 15 sterile surgical knife (Swann-Morton, England). The platysma was used as a reference for the anatomic layout.
- e—immediate application of the test composition inside the wound with a single slow movement from one end of the wound to the other. The composition was preheated in a glass dish on a heating plate set at 47° C. The temperature was taken in a control round-bottomed-flask containing water. Immediately after the incision, an amount of test composition was put in a dish using a fine chemist's spatula (3 mm wide and 1 mm thick) for the application,
- f—the 2 sides of the wound were brought together with the fingers for 30 seconds. The superficial excess test composition was removed with a compress,
- g—placing of 3 adhesive strips (Steri-strip).

The remaining five guinea pigs selected at random form the control group. They underwent an incision followed by a suture.

The surgical protocol was identical to that described above, except that after step "e", each guinea pig is sutured with single thread Proléne Bleu 4/0 equipped with a P3 curved needle, with a cross-section of 13 mm.

The suture of the incision was carried out as follows:

guinea-pig 6: 2 stitches, guinea-pig 7: 2 stitches, guinea pig 8: 3 stitches, guinea-pig 9: 2 stitches, guinea-pig 10: 3 stitches.

After the operation, each guinea pig was put back in its cage, woke up less than 5 minutes after the operation, and then was free to move about.

The wounds were locally disinfected every day with yellow Bétadine. The wounds were photographed at T=1 d; T=3 d and T=10 d.

After six days, the stitches were removed under general anaesthetic.

The aesthetic quality of the scars was assessed in blind conditions by an emergency physician used to the practice and monitoring of sutures, with the help of a visual analogue scale. The results between the two groups were compared using a Mann and Whitney non-parametric one-direction test at T=10 d (the significance threshold is set at 5%).

The guinea pigs were sacrificed by intra-peritoneal injection of a solution of Phenobarbital after eleven days in the "adhesive" group and after twelve days in the "suture" group.

Two excision-biopsies were carried out per guinea pig: a healthy skin control and one globally including the scar.

The samples were put in 10% formol solution while waiting for the anatomy-pathology analysis.

The following results were obtained.

The total duration of the operations was 1 hour between the first and last guinea pig in each group.

Several observations were noted:
- a—at T=1 d, guinea pig 6 spontaneously lost its three threads and guinea-pigs 8 and 10 spontaneously lost one thread at T=5 d.

The adhesive strips in all guinea pigs in the adhesive group (composition 1) spontaneously came off after 24 hours,
- b—no local or general infections were noted,
- c—from a blind tactile point of view, the scars on polymers were soft and not rough, as opposed to the scars with thread,
- d—the aesthetic quality of each wound at T=10 d was assessed in ions with a visual analogue scale (0–200) and the results obtained are Table II.

TABLE II

| Guinea-pig n = 5 | Composition 1 (score) | | Guinea-pig n = 5 | Thread suture (score) |
|---|---|---|---|---|
| 1 | 125 | | 6 | 141 |
| 2 | 190 | | 7 | 121 |
| 3 | 196 | | 8 | 180 |
| 4 | 168 | | 9 | 90 |
| 5 | 179 | | 10 | 80 |
| Median | 179 | p = 0.0476 | | 121 |
| minimum | 125 | | | 80 |
| maximum | 196 | | | 180 |

The statistical analysis of the aesthetic quality of the scars (visual analogue scale) after removal of the stitches on day 10, reveals a statistically significant difference (p=0.0476) in favour of the methylidene malonate composition over that of the suture thread.

No infection is noted among the two groups during the study.

The same in vivo study has been carried out with compositions 6, 8, 9, 10, 11, 12, 13 and 14.

The experimental protocol used in this study was the same as described above, the suture of the incision was carried out with three stitches for each guinea pig of the control group.

The results reported in Table III relate to the aesthetic quality of the wounds at T=21 d, as assessed in blind conditions with the help of a visual analogue scale (0–200).

The statistical analysis of these results reveals a statistically significant difference (p=0.0005) in favour of the methylidene malonate-based compositions over that of the suture thread.

The scars with threads are always penalised by a "ladder rung" aspect.

TABLE III

| COMPO- SITION No. | AESTHETIC QUALITY OF THE GLUED WOUND (score 1200) | AESTHETIC QUALITY OF THE SUTURED WOUND (score/200) |
|---|---|---|
| 6 | 192 | 175 |
| 8 | 189 | 168 |
| 9 | 184 | 155 |
| 10 | 183 | 162 |
| 11 | 175 | 172 |
| 12 | 178 | 155 |
| 13 | 183 | 169 |
| 14 | 169 | 160 |

An anatomy-pathology study was carried out:
on the one hand, to verify any inflammatory risks due to the decomposition products of the polymethylidene malonate,
on the other hand, to control the bioresorbent nature of the methylidene malonate composition used.

The results obtained demonstrate that, from a histological point of view, the behaviour of the methylidene malonate compositions is fully satisfactory.

What is claimed is:

1. A method for the suture of wounds, comprising applying within a wound a sufficient quantity of a biocompatible, bio-adhesive mixture comprising at least 50% by weight of a methylidene malonate-based composition containing:

40 to 100% by weight of at least one methylidene malonate of formula (I)

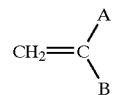

(I)

in which:
A and B independently represent a group (a) or (b):

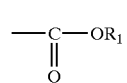

(a)

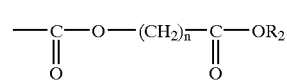

(b)

in which $R_1$ and $R_2$ independently represent a linear or branched alkyl group with 1 to 6 carbon atoms, n is an integer between 1 and 5, and at least one of A and B represents a (b) group;

and/or one or more methylidene malonate oligomers with a molecular weight less than or equal to 6,000 and including recurrent units of formula (II):

(II)

in which A and B are as defined above; and 0 to 60% by weight of at least one methylidene malonate polymer with a molecular weight greater than 6,000 and including recurrent units of formula (II).

2. A method according to claim 1, wherein in said formulae (I) and (II):

A represents a group (a) in which $R_1$ represents an alkyl group with 1 to 6 carbon atoms, and B represents a group (b) in which $R_2$ represents an alkyl group with 1 to 6 carbon atoms, and n is a number equal to 1.

3. A method according to claim 2, wherein in said formulae (I) and (II):

A represents a group (a) in which $R_1$ represents an ethyl group; and

B represents a group (b) in which $R_2$ represents an ethyl group and n is a number equal to 1.

4. A method according to claim 1, wherein said methylidene malonate-based composition contains:

50 to 90% by weight of at least one methylidene malonate oligomer with a molecular weight less than or equal to 6,000 and including recurrent units of formula (II), and 10 to 50% by weight of at least one methylidene malonate polymer with a molecular weight greater than 6,000, said mixture having a glass transition temperature that is less than or equal to 0° C.

5. A method according to claim 4, wherein the methylidene malonate-based composition contains:

55 to 65% by weight of at least one methylidene malonate oligomer with a molecular weight that less than or equal to 3,000 and consisting of recurrent units of formula (II), and 35 to 45% by weight of at least one methylidene malonate polymer with a molecular weight greater than 6,000.

6. A method according to claims 5, wherein the methylidene malonate-based composition contains:

55 to 65% by weight of at least one methylidene malonate oligomer with a molecular weight between 300 and 1,000 and including recurrent units of formula (II), and 35 to 45% by weight of at least one methylidene malonate polymer with a molecular weight between 12,000 and 25,000.

7. A method according to claim 4, wherein said mixture contains up to 50% by weight of at least one constituent other than the methylidene malonate-based composition, and selected from the group consisting of:

polycyanoacrylates;

polyalkylmethacrylates;

biocompatible polyurethanes;

polyoxyalkylenes;

polyaminoacids;

polylactates;

polylactate-co-glycolates; and polyvinylalcohols.

8. A method according to claim 7, wherein said at least one constituent is present, at least in part, in the form of monomer units associated with the methylidene malonate units of formula (II), in a copolymer.

9. A method according to claim 4, wherein said mixture contains up to 20% by weight of at least one constituent other than the methylidene malonate-based composition, and selected from the group consisting of:

polycyanoacrylates;

polyalkylmethacrylates;

biocompatible polyurethanes;

polyoxyalkylenes;

polyaminoacids;

polylactates;

polylactate-co-glycolates; and polyvinylalcohols.

10. A method according to claim 1, wherein said mixture contains at least 90% by weight of said methylidene malonate-based composition.

11. A method for the suture of wounds comprising:

a) preheating to a temperature above its softening temperature, a biocompatible, bioadhesive mixture comprising at least 50% by weight of a methylidene malonate-based composition containing:

40 to 100% by weight of at least one methylidene malonate of formula (I)

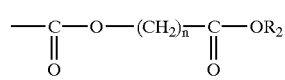
(I)

in which:

A and B independently represent a group (a) or (b):

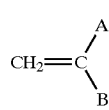
(a)

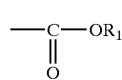
(b)

in which $R_1$ and $R_2$ independently represent a linear or branched alkyl group with 1 to 6 carbon atoms, n is an integer between 1 and 5, and at least one of A and B represents a (b) group;

and/or one or more methylidene malonate oligomers with a molecular weight less than or equal to 6,000 and including recurrent units of formula (II):

(II)

in which A and B are as defined above; and 0 to 60% by weight of at least one methylidene malonate polymer with a molecular weight greater than 6,000 and including recurrent units of formula (II);

b) applying within a wound a sufficient quantity of the preheated mixture.

12. A method according to claim 11, wherein the methylidene malonate-based composition contains:

50 to 90% by weight of at least one methylidene malonate oligomer with a molecular weight less than or equal to 6,000 and consisting of recurrent units of formula (II), and 10 to 50% by weight of at least one methylidene malonate polymer with a molecular weight greater than 6,000, said mixture having a glass transition temperature that s less than or equal to 0° C.

13. A method according to claim 12, wherein the methylidene malonate-based composition contains:

55 to 65% by weight of at least one methylidene malonate oligomer with a molecular weight that less than or equal to 3,000 and including recurrent units of formula (II), 35 to 45% by weight of at least one methylidene malonate polymer with a molecular weight greater than 6,000.

14. A method according to claim 13, wherein the methylidene malonate-based composition contains:

55 to 65% by weight of at least one methylidene malonate oligomer with a molecular weight between 300 and 1,000 and including recurrent units of formula (II), and 35 to 45% by weight of at least one methylidene malonate polymer with a molecular weight between 12,000 and 25,000.

15. A method according to claim 12, wherein said mixture contains up to 20% by weight of at least one constituent other than the methylidene malonate-based composition, and selected from the group consisting of:

polycyanoacrylates;

polyalkylmethacrylates;

biocompatible polyurethanes;

polyoxyalkylenes;

polyaminoacids;

polylactates;

polylactate-co-glycolates; and polyvinylalcohols.

16. A method according to claim 15, wherein said at least one constituent is present, at least in part, in the form of monomer units associated with the methylidene malonate units of formula (II), in a copolymer.

17. A method according to claim 11, wherein said mixture contains at least 90% by weight of said methylidene malonate-based composition.

18. A material comprising at least 90% by weight of a methylidene malonate composition containing:
50 to 90% by weight of at least one methylidene malonate oligomer with a molecular weight less than or equal to 6,000 and including recurrent units of formula (II):

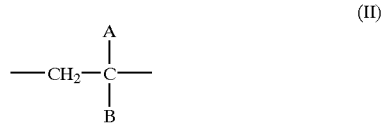
(II)

in which:
A and B independently represent a group (a) or (b):

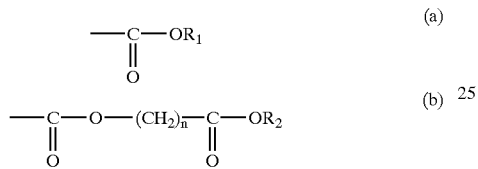
(a)
(b)

in which $R_1$ and $R_2$ independently represent a linear or branched alkyl group with 1 to 6 carbon atoms, n is an integer between 1 and 5, and at least one of A and B represents a (b) group; and 10 to 50% by weight of at least one methylidene malonate polymer with a molecular weight greater than 6,000,
said material having a glass transition temperature that is less than or equal to 0° C.

19. A material which comprising at least 90% by weight of a methylidene malonate composition containing:
50 to 90% by weight of at least one methylidene malonate oligomer with a molecular weight less than or equal to 3,000 and including recurrent units of formula (II):

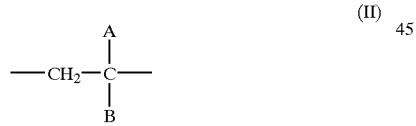
(II)

in which:
A and B independently represent a group (a) or (b):

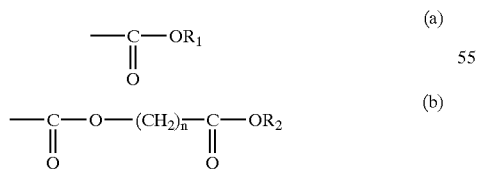
(a)
(b)

in which $R_1$ and $R_2$ independently represent a linear or branched alkyl group with 1 to 6 carbon atoms, n is an integer between 1 and 5, and at least one of A and B represents a (b) group; and 10 to 50% by weight of at least one methylidene malonate polymer with a molecular weight greater than 6,000,
said material having a glass transition temperature that is less than or equal to 0° C.

20. A material according to claim 19, wherein the methylidene malonate-based composition contains:
55 to 65% by weight of at least one methylidene malonate oligomer with a molecular weight that less than or equal to 3,000 and including recurrent units of formula (II), and
35 to 45% by weight of at least one methylidene malonate polymer with a molecular weight greater than 6,000.

21. Material according to claim 20, wherein the methylidene malonate-based composition contains:
55 to 65% by weight of at least one methylidene malonate oligomer with a molecular weight between 300 and 1,000 and including recurrent units of formula (II), and
35 to 45% by weight of at least one methylidene malonate polymer with a molecular weight between 12,000 and 25,000.

22. A material according to claim 19, wherein the methylidene malonate-based composition contains:
55 to 65% by weight of at least one methylidene malonate oligomer with a molecular weight that less than or equal to 3,000 and including recurrent units of formula (II), and
35 to 45% by weight of at least one methylidene malonate polymer with a molecular weight greater than 9,000.

23. A material for the suture of wounds, comprising a biocompatible, bio-adhesive mixture comprising at least 50% by weight of a methylidene malonate-based composition containing:
40 to 100% by weight of at least one methylidene malonate of formula (I)

(I)

in which:
A and B independently represent a group (a) or (b):

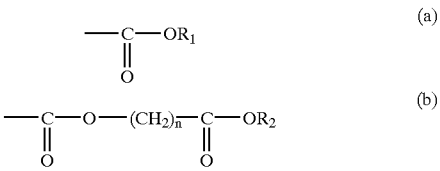
(a)
(b)

in which $R_1$ and $R_2$ independently represent a linear or branched alkyl group with 1 to 6 carbon atoms, n is an integer between 1 and 5, and at least one of A and B represents a (b) group;
and/or at least one methylidene malonate oligomer with a molecular weight less than or equal to 6,000 and including recurrent units of formula (II):

(II)

in which A and B are as defined above;
0 to 60% by weight of at least one methylidene malonate polymer with a molecular weight greater than 6,000 and including recurrent units of formula (II).

24. A material according to claim 23, wherein in said formulae (I) and (II):

A represents a group (a) in which $R_1$ represents an alkyl group with 1 to 6 carbon atoms, B represents a group (b) in which $R_2$ represents an alkyl group with 1 to 6 carbon atoms, and n is a number equal to 1.

25. A material according to claim 24, wherein in said formulae (I) and (II):

A represents a group (a) in which $R_1$ represents an ethyl group; and

B represents a group (b) in which $R_2$ represents an ethyl group and n is a number equal to 1.

26. A material according to claim 23, wherein the methylidene malonate-based composition contains:

50 to 90% by weight of at least one methylidene malonate oligomer with a molecular weight less than or equal to 6,000 and consisting of recurrent units of formula (II), and 10 to 50% by weight of at least one methylidene malonate polymer with a molecular weight greater than 6,000, said material having a glass transition temperature that is less than or equal to 0° C.

27. A material according to claim 26, wherein the methylidene malonate-based composition contains:

55 to 65% by weight of at least one methylidene malonate oligomer with a molecular weight that less than or equal to 3,000 and including recurrent units of formula (II), and 35 to 45% by weight of at least one methylidene malonate polymer with a molecular weight greater than 6,000.

28. A material according to claim 27, wherein the methylidene malonate-based composition contains:

55 to 65% by weight of at least one methylidene malonate oligomer with a molecular weight between 300 and 1,000 and including recurrent units of formula (II), and 35 to 45% by weight of at least one methylidene malonate polymer with a molecular weight between 12,000 and 25,000.

29. A material according to claim 26, comprising up to 50% by weight of at least one constituent other than said methylidene malonate-based composition, and selected from the group consisting of:

polycyanoacrylates;

polyalkylmethacrylates;

biocompatible polyurethanes;

polyoxyalkylenes;

polyaminoacids;

polylactates;

polylactate-co-glycolates; and polyvinylalcohols.

30. A material according to claim 29, wherein said at least one constituent is present in the form of monomer units associated with the methylidene malonate units of formula (II), in a copolymer.

31. A material according to claim 26, comprising up to 20% by weight of at least one constituent other than said methylidene malonate-based composition, and selected from the group consisting of:

polycyanoacrylates;

polyalkylmethacrylates;

biocompatible polyurethanes;

polyoxyalkylenes;

polyaminoacids;

polylactates;

polylactate-co-glycolates; and polyvinylalcohols.

32. A material according to claim 23, comprising at least 90% by weight of said methylidene malonate-based composition .

* * * * *